United States Patent
Sibai (10) Patent No.: US 9,239,297 B2
(45) Date of Patent: Jan. 19, 2016

(54) OUTER SURFACE INSPECTING ROBOT WITH FLIPPING OVER FLANGE MECHANISM

(71) Applicant: Saudi Arabian Oil Company, Dhahran (SA)

(72) Inventor: Fadi Sibai, Dhahran Hills (SA)

(73) Assignee: Saudi Arabian Oil Company, Dhahran (SA)

(*) Notice: Subject to any disclaimer, the term of this patent is extended or adjusted under 35 U.S.C. 154(b) by 232 days.

(21) Appl. No.: 13/915,110

(22) Filed: Jun. 11, 2013

(65) Prior Publication Data

US 2014/0146161 A1    May 29, 2014

Related U.S. Application Data

(60) Provisional application No. 61/773,685, filed on Mar. 6, 2013, provisional application No. 61/729,697, filed on Nov. 26, 2012.

(51) Int. Cl.
*G01N 21/95* (2006.01)
*B25J 5/00* (2006.01)
*B62D 57/028* (2006.01)

(52) U.S. Cl.
CPC .......... *G01N 21/95* (2013.01); *B25J 5/007* (2013.01); *B62D 57/028* (2013.01)

(58) Field of Classification Search
CPC ........ G01N 21/95; B25J 5/007; B62D 57/028
See application file for complete search history.

(56) References Cited

U.S. PATENT DOCUMENTS

| 8,083,013 | B2 | 12/2011 | Bewley et al. |
| 8,316,972 | B2 | 11/2012 | Hutcheson et al. |
| 2002/0083789 | A1* | 7/2002 | Sundaresan et al. ............ 74/512 |

(Continued)

FOREIGN PATENT DOCUMENTS

| EP | 2 522 469 A1 | 11/2012 |
| JP | S57 194171 A | 11/1982 |

(Continued)

OTHER PUBLICATIONS

Fukuda et al. "Automated Pipeline Inspection Robot in Construction" 5th International Symposium on Robotics in Construction; Tokyo, Japan; Jun. 6-8, 1988; pp. 887-896.
PCT International Search Report and the Written Opinion of the International Searching Authority dated Feb. 12, 2014; International Application No. PCT/US2013/071890; International File Date: Nov. 26, 2013.

(Continued)

*Primary Examiner* — Jay Patel
*Assistant Examiner* — Joseph Suh
(74) *Attorney, Agent, or Firm* — Bracewell & Giuliani LLP; Constance Gall Rhebergen (57) ABSTRACT

A pipe inspecting robot having a body, first and second independently articulating legs, and first and second leg motors for controlling the first and second articulating legs. The robot also has first and second pairs of wheels attached to the first and second legs at an opposite end of the legs from the body. The leg motors are configured so that when the first pair of wheels encounters an obstacle, the second leg motor rotates the second leg upward away from the surface of the pipeline and radially around the body until the second pair of wheels contacts the surface of the pipeline on an opposite side of the obstacle. Then the first leg motor rotates the first leg upward away from the surface of the pipeline and radially around the body until the first pair of wheels contacts the surface of the pipeline.

20 Claims, 7 Drawing Sheets

(56) References Cited

U.S. PATENT DOCUMENTS

2007/0109403 A1* 5/2007 Lortie .............................. 348/85
2007/0235234 A1* 10/2007 De Kruijf ..................... 180/65.2
2009/0120215 A1* 5/2009 Jacobson et al. ............. 73/865.8

FOREIGN PATENT DOCUMENTS

| JP | H61 146686 A | 7/1986 |
| JP | H05 261681 A | 10/1993 |

OTHER PUBLICATIONS

Fukuda, T., et al., Path Planning and Control of Pipeline Inspection and Maintenance Robot; Industrial Electronics Society, 1988; IECON 1988; Proceedings; 14th Annual Conference of, IEEE; Oct. 24, 1988; pp. 38-43.

Yukawa, T., et al., Magnetic Part Design of Pipe-Surface Inspection Robot; Industrial Electronics Society, 2006; IECON 2006; 32nd Annual Conference on, IEEE, Piscataway, NJ; Nov. 1, 2006; pp. 3957-3962.

* cited by examiner

OUTER SURFACE INSPECTING ROBOT WITH FLIPPING OVER FLANGE MECHANISM

CROSS REFERENCE TO RELATED APPLICATIONS

This application claims priority to and the benefit of U.S. Provisional Application Ser. Nos. 61/729,697 and 61/773,685, which were filed Nov. 26, 2012 and Mar. 6, 2013, respectively, the fill disclosures of which are hereby incorporated herein by reference.

BACKGROUND OF INVENTION

1. Field of the Invention

The present technology relates to robotic inspection of outer pipe surfaces and to movement of a robotic inspection device past obstacles connected to outer pipe surfaces.

2. Description of the Related Art

Pipelines extending over long distances across land or open terrain are inspected externally by both manual human inspection and internally by pipeline pigs and other in-pipe tools. There exist a number of systems for inspecting various types of pipelines, including oil and gas pipelines extending over land, underground, undersea, and over other terrain.

Pipeline inspection gauges (pigs) typically pass through a pipeline by a flow of fluid that pushes the pig. The pigs often contain instrumentation that inspects the internal surface of the pipeline. Pigs also are used to push sediment or other obstacles through the pipeline to keep the line clear. Ultrasonic and electro-magnetic sensors have seen use on pipeline pigs to develop images of internal pipeline surfaces over long distances. This data can be visually reviewed or analyzed by computer algorithms to detect pipeline damage or sediment build-up within a pipeline.

SUMMARY OF THE INVENTION

One embodiment of the present technology provides a pipe inspecting robot for traveling along the surface of a pipeline. The robot includes a body, first and second independently articulating legs attached to the body, first and second leg motors in controlling communication with the first and second articulating legs, respectively, and first and second pairs of wheels attached to the first and second a articulating legs, respectively, at an opposite end of the legs from the body. In addition, the first and second leg motors are configured so that when the first pair of wheels encounters an obstacle, the second leg motor rotates the second leg upward away from the surface of the pipeline and radially around the body until the second pair of wheels contacts the surface of the pipeline on an opposite side of the obstacle, after which the first leg motor rotates the first leg upward away from the surface of the pipeline and radially around the body until the first pair of wheels contacts the surface of the pipeline, thereby causing the robot to pass over the obstacle.

In the pipe inspecting robot, the first and second pairs of wheels can be attached to the first and second articulating legs by first and second wheel hubs, respectively, and the wheel hubs can contain at least one wheel motor to power the wheels. Furthermore, each wheel can be powered by a separate wheel motor, and the course of the robot can be adjusted by increasing or decreasing the speed of each wheel with its corresponding wheel motor.

In addition, body of the robot can contain at least one device selected from the group consisting of a control circuit, a communication circuit, a global positioning system (GPS) circuit, a GPS antenna, a camera, a camera circuit, and a battery pack. The robot can also include a downward facing camera attached to the body for collecting data about the surface condition of the pipeline and for guiding the robot. In some embodiments, the robot can be autonomous. In other embodiments, it can be remote controlled. Furthermore, pins can be attached to the body and can have an extended and a retracted position. When in the extended position, the pins can lock the position of the legs relative to the body. When in the retracted position, the pins can allow the legs to articulate relative to the body.

The robot can further include a radial arm attached to the body and extending outward from the body around a portion of the circumference of the pipe, the radial arm having a camera for inspecting the surface of the pipe. In addition, the robot can have a radial arm extension slidably attached to the radial arm and configured to extend still further around the circumference of the pipe.

An alternate embodiment of the present technology provides a pipeline inspection robot having a body, first and second legs attached to the body, first and second wheels attached to the first and second legs, respectively, at an opposite end of the legs from the body, and a radial arm attached to the body and extending outward from the body around a portion of the circumference of the pipeline, the radial arm having a camera for inspecting the surface of the pipeline. The robot can also include a radial arm extension slidably attached to the radial arm and configured to extend further around the circumference of the pipeline than the radial arm.

In addition, the robot can have first and second leg motors in controlling communication with the first and second legs, respectively, the first and second leg motors configured so that when the first wheels encounters an obstacle the second leg motor rotates the second leg upward away from the surface of the pipeline and radially around the body until the second wheel contacts the surface of the pipeline on an opposite side of the obstacle, after which the first leg motor rotates the first leg upward away from the surface of the pipeline and radially around the body until the first pair of wheels contacts the surface of the pipeline, thereby causing the robot to pass over the obstacle. Furthermore, the first and second wheels can be attached to the first and second legs by first and second wheel hubs, respectively, wherein the wheel hubs contain a separate wheel motor for each wheel, and wherein the course of the robot can be adjusted by increasing or decreasing the speed of each wheel with its corresponding wheel motor.

In certain embodiments, the robot can include a downward facing camera attached to the body for collecting data about the surface condition of the pipeline and for guiding the robot. In addition, the robot can be either autonomous or remote controlled. Furthermore, the robot can include pins attached to the body and having an extended and a retracted position, wherein when in the extended position the pins lock the position of the legs relative to the body, and when in the retracted position the pins allow the legs to articulate relative to the body.

Also disclosed herein is a method of inspecting a pipeline. The method includes providing a robot inspection device that has a body, and first and second wheel assemblies that articulate fully around a circumference of the body and have wheels on an end distal from the body. The method includes the steps of urging the device along the pipeline and adjacent to an obstacle on the pipeline so that one of the wheel assemblies is proximate the obstacle, articulating the body with respect to the proximate wheel assembly and articulating a wheel assembly distal from the obstacle with respect to the body so that wheels on the distal wheel assembly orbit over the pipeline and land onto the pipeline on a side of the obstacle opposite the proximate wheel assembly, and articulating the body with respect to the distal wheel assembly and articulating the proximate when assembly with respect to the body so that wheels on the proximate wheel assembly land on the pipeline on a side of the distal wheel assembly distal from the obstacle. In some embodiments, the method can include the step of detecting the obstacle using a device attached to the robot body and selected from the group consisting of a camera, a global positioning system (GPS), and a proximity sensor.

BRIEF DESCRIPTION OF THE DRAWINGS

So that the manner in which the above-recited features, aspects and advantages of the technology, as well as others that will become apparent, are attained and can be understood in detail, more particular description of the technology briefly summarized above can be had by reference to the embodiments thereof that are illustrated in the drawings that form a part of this specification. It is noted, however, that the appended drawings illustrate only preferred embodiments of the technology that are, therefore, not to be considered limiting of the technology's scope, for the technology can admit to other equally effective embodiments.

DETAILED DESCRIPTION

Figure 1:
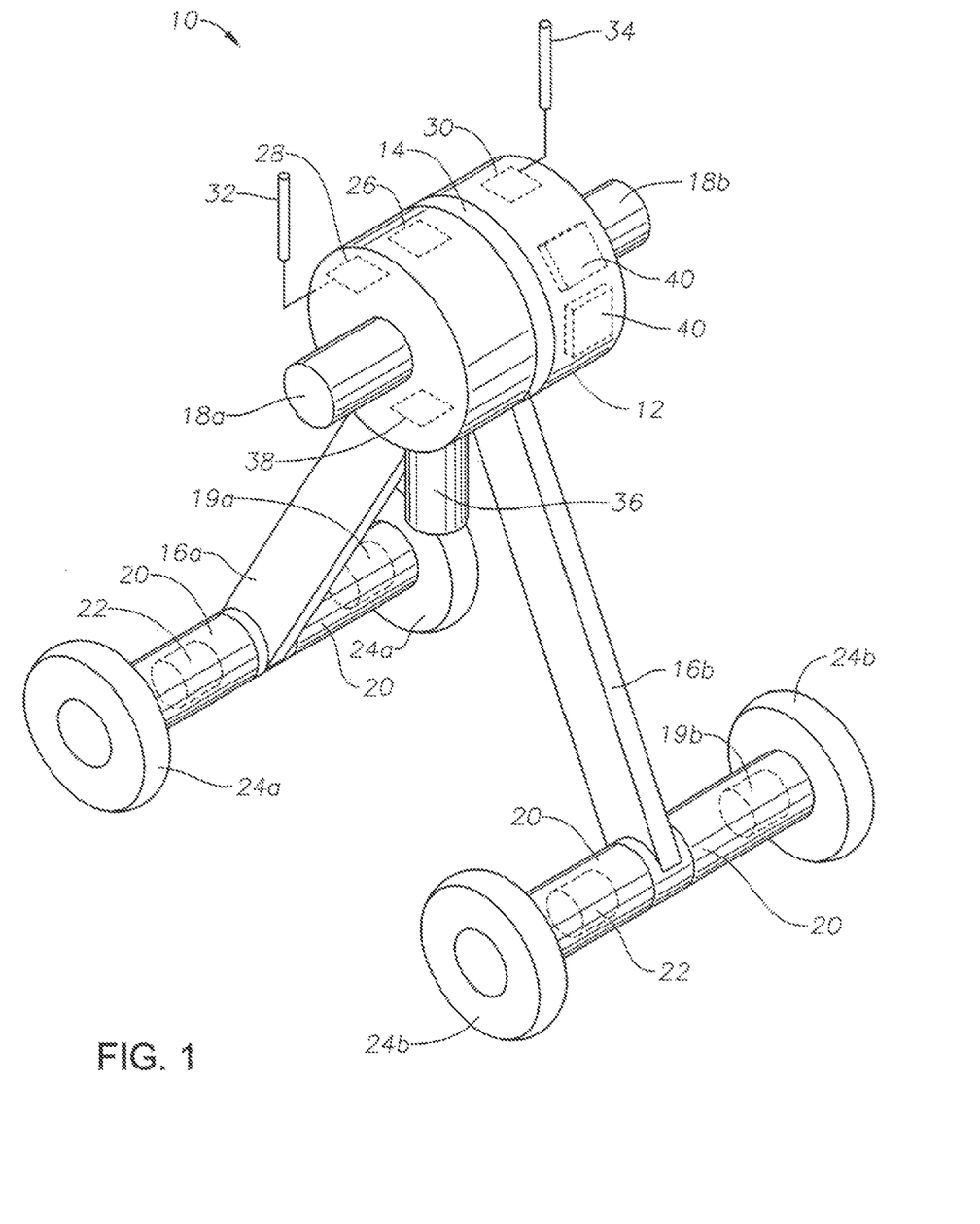
FIG. 1 is a perspective view of a pipeline inspection robot in accordance with an embodiment of the present technology.

FIG. 1 illustrates an embodiment of a pipeline inspection system that includes a pipeline inspection robot 10. The pipeline inspection robot 10 contains sub-systems to control the movement of the robot 10 and facilitate pipeline inspection. The robot 10 has a main external housing 12 that has a cut-out section 14 that provides for the central connection and movement of first and second articulating legs 16a, 16b. Each leg 16a, 16b is elongated and articulates about the housing 12 by the power of an individual leg motor 18a, 18b. Lower ends of the articulating legs 16a, 16b connect to elongate wheel hubs 20 that extend perpendicular to the legs 16a, 16b. Each leg 16a, 16b articulates about its respective hub 20 by the power of an individual hub leg motor 19a, 19b). In one embodiment, the wheel hubs 20 can house wheel motors 22 to power a first and second set of wheels 24a, 24b that connect to the wheel hubs 20. First and second set of wheels 24a, 24b correspond to first and second legs 16a, 16b, respectively. In some embodiments, such as that shown in FIG. 1, each individual wheel 24a, 24b can have an individual wheel motor 22 that powers only that particular wheel. In other embodiments, each set of wheels 24 can share a wheel motor 22.

The main external housing 12 of the robot 10 can house other components that facilitate the autonomous control or remote control of the robot 10. For example, in an embodiment, the housing 12 can contain control circuitry 26, communication circuitry 28, GPS circuitry 30, a communication antenna 32, a GPS antenna 34, a camera system 36, camera circuitry 38, and other camera connected hardware to store camera images. The housing 12 can contain one or more battery packs 40 to power the various robot motors and also the control, camera, OPS, and communication systems of the robot 10.

Figure 2:
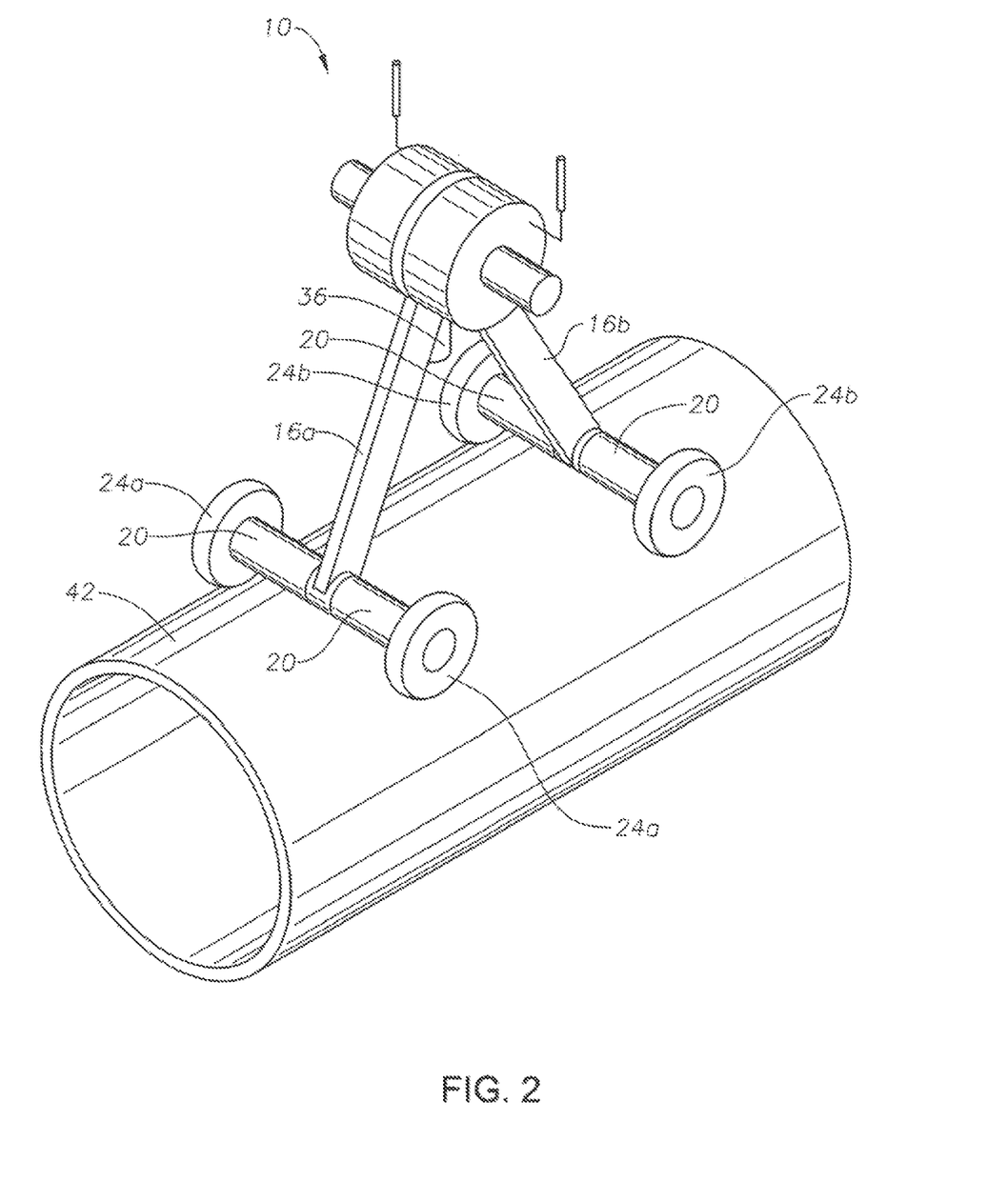
FIG. 2 is an alternate perspective view of the pipeline inspection robot of FIG. 1 sitting atop a pipeline.

FIG. 2 illustrates an alternative perspective view of the pipeline inspection system showing the pipeline inspection robot 10 sitting atop a pipeline 42 in accordance with an embodiment of the present technology. The wheels 24a, 24b are aligned in a direction that allows the robot 10 to travel on top of the pipeline 42. The wheel hubs 20 are correspondingly positioned substantially perpendicular to the longitudinal axis of the pipeline 42. The camera system 36 of the robot 10 has a downward facing camera. This camera allows the robot to collect data regarding the surface condition of the pipeline 42, and also allows the robot 10 to make position adjustments as the robot 10 travels along the pipeline 42. Position adjustments can be made by the robot 10 autonomously or under the control of a remote user. In one example, when under autonomous or self-control, the robot 10 monitors the position of the robot 10 on the pipeline 42 using the camera system 36. Image data collected by the camera system 36 is analyzed by the control circuitry 26, which can make position adjustments to the course the robot 10 is taking using the various wheel motors 22. In some embodiments, selectively operating the housing leg motors 18a, 18b, or hub leg motors 19a, 19b, can also make position adjustments that change the course of the robot 10 on the pipeline 42. In some embodiments, the GPS data received by the GPS circuitry 30 can also be used in autonomous positioning algorithms run by the control circuitry 26 of the robot 10. The GPS location data determined by the GPS circuitry 30 can be compared to known pipeline location data in the storage medium of the control circuitry 26. By comparing the current GPS position to a known pipeline position and contour, the robot's control circuitry 26 can plot a course that keeps the robot 10 moving down a central location on the pipeline 42 substantially parallel to the axis of the pipeline 42.

Figure 3:
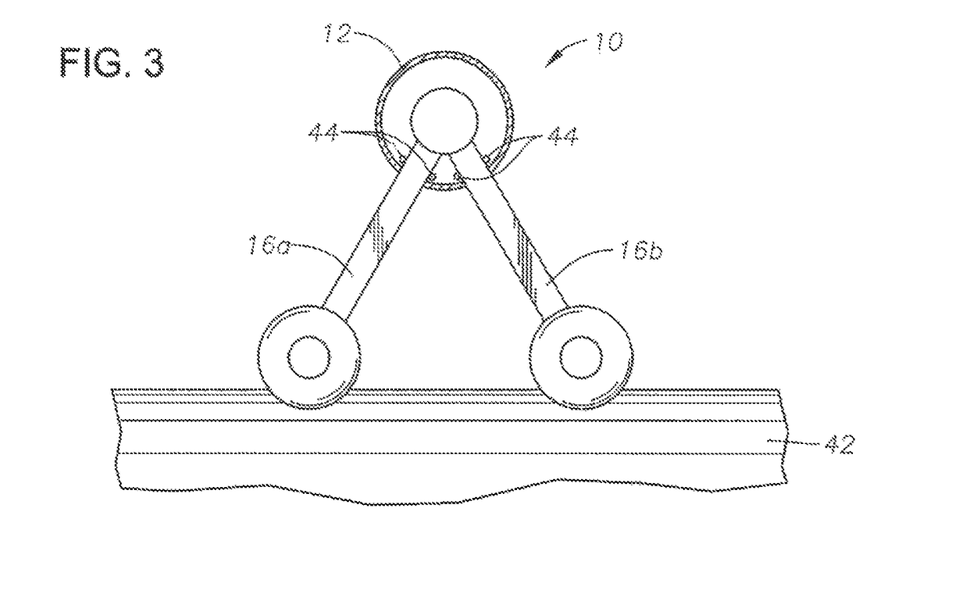
FIG. 3 is a side elevation view of the pipeline inspection robot of FIG. 1 on top of a pipe.

FIG. 3 illustrates a side elevation view of the pipeline inspection system showing the pipeline inspection robot 110, with one side of the main external housing 12 removed, and the robot 10 on top of a pipeline 42 in accordance with an embodiment of the present technology. In an embodiment, the robot 10 can have a set of retractable leg locking pins 44 that extend laterally from the main external housing 12 of the robot 10 and into selective interference with legs 16a, 16b. The retractable leg locking pins 44 can serve to lock the articulating legs 16a, 16b of the robot 10 into a traveling position, and to stabilize the legs 16a, 16b when the robot 10 is traveling along the pipeline 42. The retractable leg locking pins 44 can be retracted back into the main external housing 12 of the robot 10 when the robot 10 encounters an obstacle that the robot 10 needs to flip around, as shown, for example, in FIG. 5 and discussed below. Optionally, control circuitry 26 controls insertion and retraction of the locking pins 44.

Figure 4:
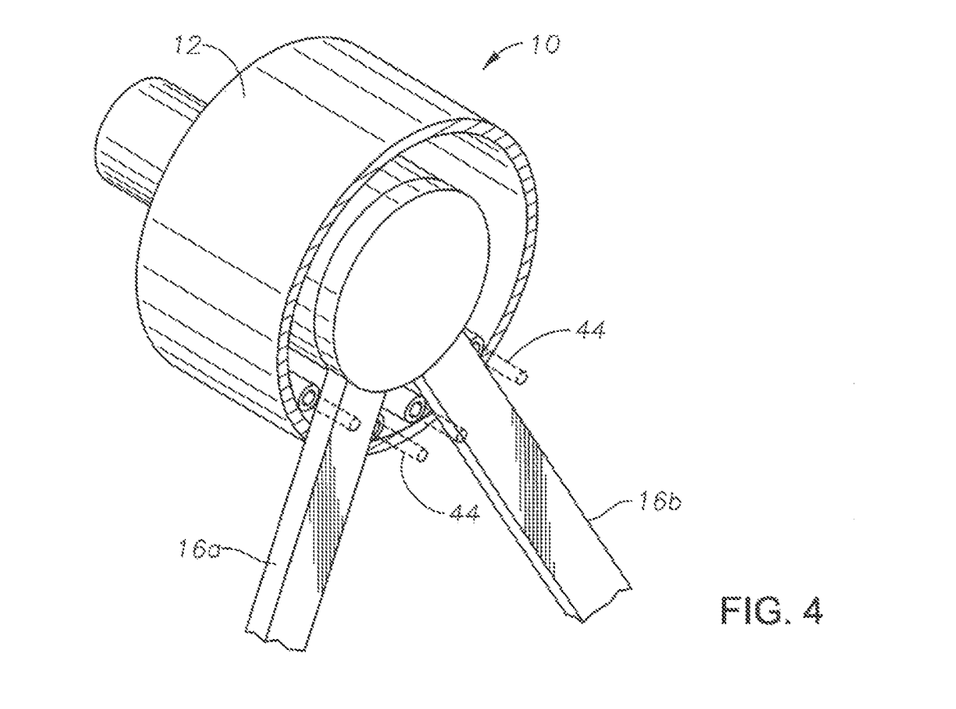
FIG. 4 is an enlarged perspective view of the pipeline inspection robot.

FIG. 4 illustrates an enlarged perspective view of the pipeline inspection system showing an upper portion of the pipeline inspection robot 10 with one side of the main external housing 12 removed in accordance with an embodiment of the present technology. In an embodiment, the retractable leg locking pins 44 can extend and retract electromagnetically, by mechanical means, or otherwise, The main external housing 12 can hold electromagnets (not shown) or a mechanical structure that connects to the locking pins 44, and that can both extend and retract the pins 44. The pins 44 can be housed in one side of the external housing 12 or can have, for example, some pins in one side of the housing 12 and some pins in the other side of the housing 12.

Figure 5:
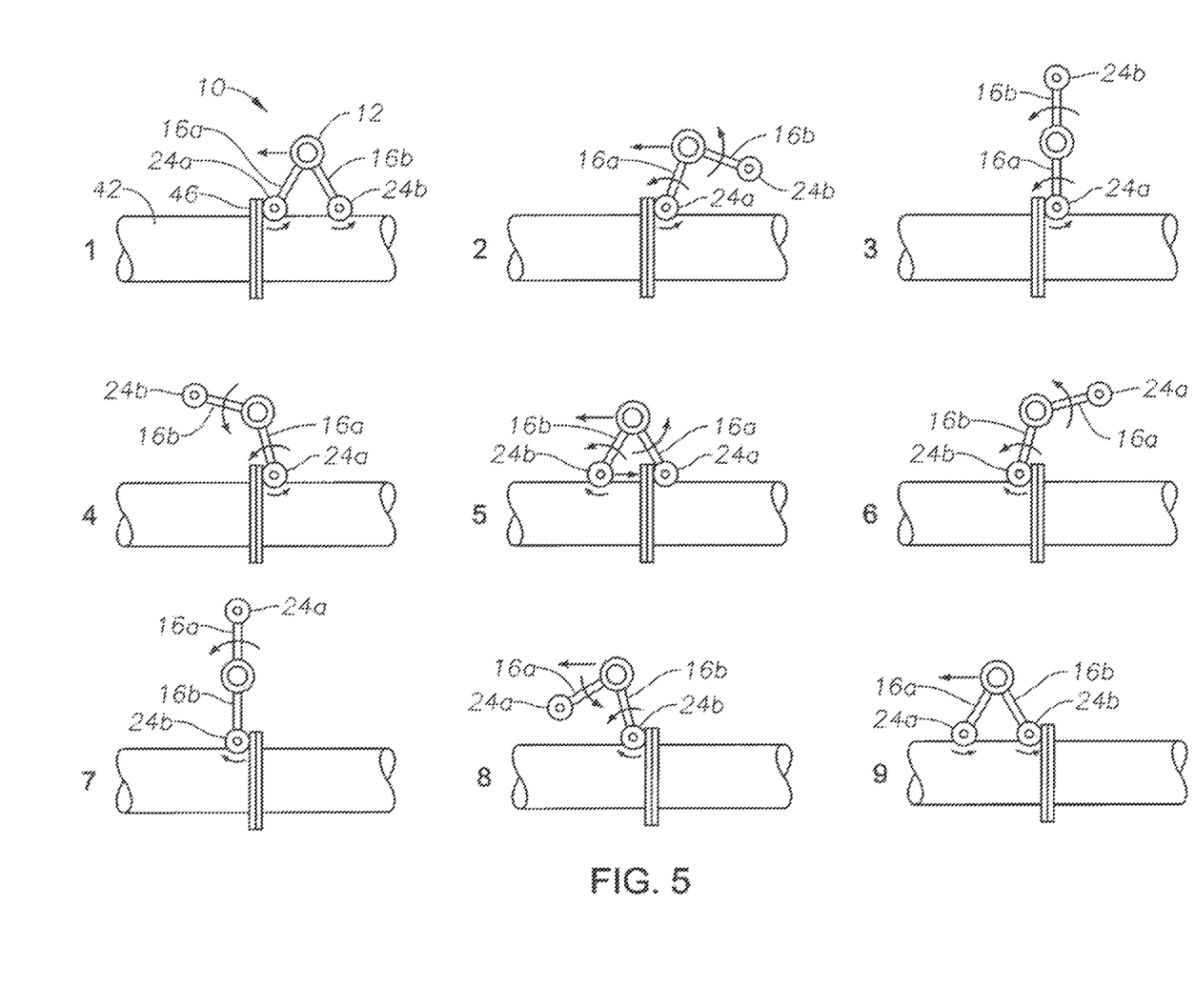
FIG. 5 are side elevation views of the pipeline inspection robot of FIG. 2 in various positions of negotiating an obstacle on the pipeline.

FIG. 5 illustrates a side elevation view of an embodiment of the pipeline inspection system where the pipeline inspection robot 10 manifests various positions as it negotiates an obstacle on the pipeline 42. As the robot 10 travels down the pipeline 42, the robot 10 can encounter an obstacle such as a flange 46, which introduces discontinuity on all outer surface of the pipeline 42, and that prevents smooth forward movement of the robot 10. The robot 10 can detect an obstacle or stalled movement in a number of ways, such as by using the camera system 36, the GPS 30, feedback from the wheel motors 22, by sensing forces exerted on the wheels 24a, 24b, or via proximity sensors. Proximity sensors can include optical/laser sensors or ultrasound sensors. The camera system 36, along with the control circuitry 26, can detect lack of forward progress of the robot 10 by using image analysis or alternatively by comparing GPS location data to anticipated location based on the speed of the robot 10. The camera system 36 and GPS 30 can also be used in combination to detect that the robot has encountered an obstacle such as a flange 46. Additionally, if locations of each obstacle on a pipeline are known, the robot 10 can anticipate each obstacle and prepare to move over it at the known locations along the pipeline 42.

FIG. 5 shows multiple positions of the robot's articulating legs 16a, 16b as the robot 10 passes over a flange 46. As shown in position 1 of FIG. 5, after the robot 10 detects the flange 46, it can move the first wheels 24a against the flange 46. Then, as shown in position 2, the housing leg motor 18b attached to the second leg 16b rotates the second leg 16b counter clockwise up and away from the pipeline 42. As this happens, the second wheels 24b will lift above the pipeline 42. Meanwhile, the hub leg motor 19a attached to the first leg 16a rotates the first leg 16a in a counter clockwise direction. This simultaneous movement changes the robot 10 into an upright position, with the second leg 16b and the second wheels 24b directly above housing 12, the first leg 16a, and the first wheels 24a, as shown in position 3.

To flip over the flange 46 as shown in position 4, the housing leg motor 18b attached to the second leg 16b will lower the second leg Mb by continuing to rotate the second leg 16b in a counter clockwise direction. The hub leg motor 19a attached to the first leg 16a rotates the first leg 16a until the second wheels 24b come into contact with the pipeline 42 on the side of the flange 46 opposite first wheels 24a, as shown in position 5, so the robot 10 is straddling the flange 46. To finish clearing the flange 46, and as shown in positions 6-9, the robot repeats the steps outlined above until both the first and second wheels 24a, 24b are on the same side of the flange 46.

Figure 6:
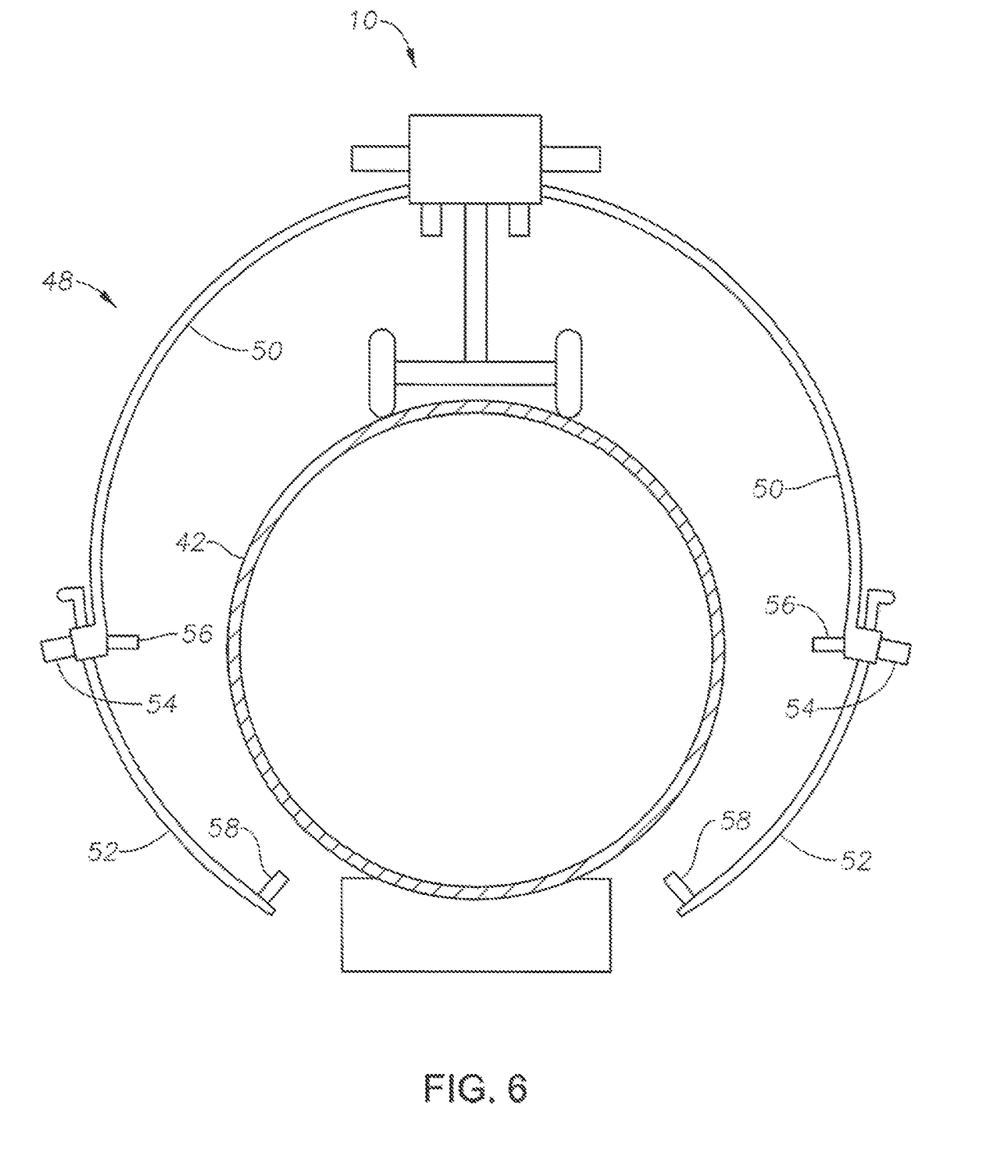
FIG. 6 is a rear elevation partial sectional view of an example embodiment of a pipeline inspection robot having an optional multiple arm side extension camera system.

FIG. 6 illustrates a rear elevation view of the pipeline inspection system showing the pipeline inspection robot 10 with an optional multiple arm side extension camera system 48. The camera system includes a set of upper partially circular arms 50, lower partially circular arm extensions 52, a set of lower arm extension motors 54, a set of upper arm cameras 56 and a set of lower arm cameras 58. Each upper arm 50 can extend about 90 degrees from opposing lateral sides of housing 12. The lower arm extensions 52 will typically extend less than 90 degrees as they normally will not extend completely to the lower side of pipeline 42, but can extend to below pipeline 42. In an embodiment, the upper circular arms 50 extend the upper arm cameras 56 along the sides of the pipeline 42 around an axis of pipeline 42. The lower circular arm extensions 52 and extension motors 54 can position the lower arm cameras 58 in multiple locations between the upper arm cameras 56 and a medial lower portion of the pipeline 42. Similar to the above described camera system 36, the cameras 56, 58 can collect image data indicating the integrity of pipeline 42. Also, the image data can be analyzed by the control circuitry 26 to make position adjustments to the course of the robot 10 using the wheel motors 22. Additionally, the camera data can be analyzed in real time or collected and analyzed later to determine the condition of the pipeline 42 and if any repairs need to be made.

Figure 7A:
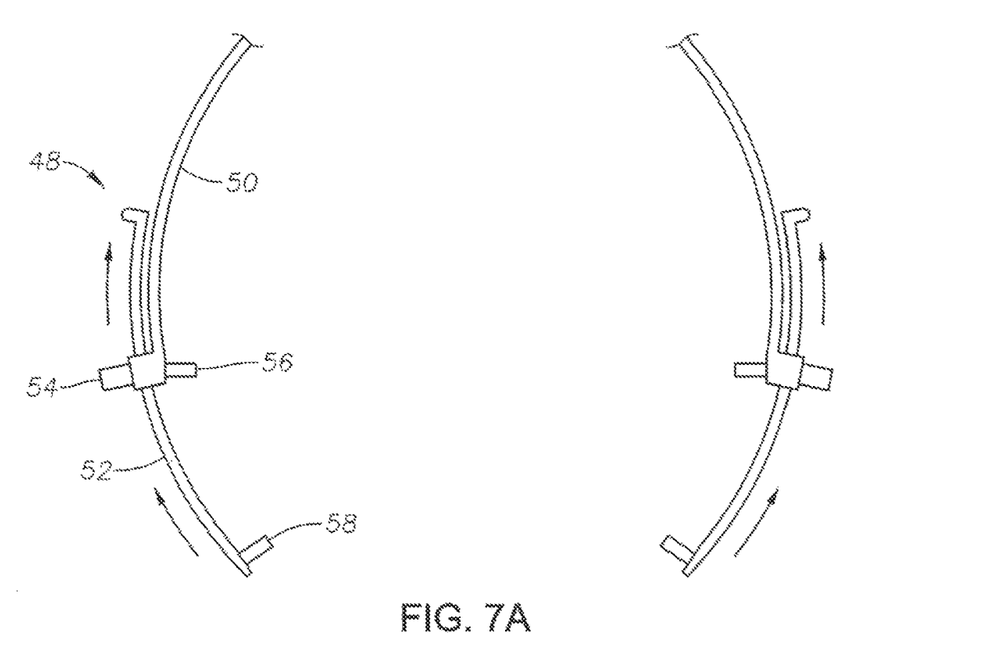
FIG. 7A is a rear elevation view of the side extension camera system of FIG. 6 with the lower camera extension arms in an extended position.
Figure 7B:
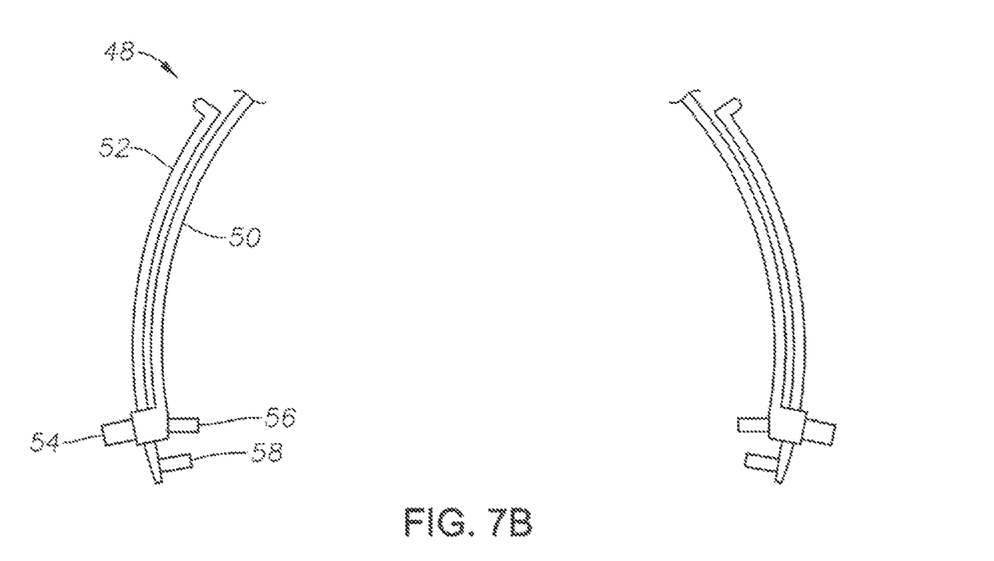
FIG. 7B is a rear elevation view of the side extension camera system of FIG. 6 with the lower camera extension arms in a retracted position.

FIGS. 7A and 7B illustrate a rear elevation view of the upper partially circular arms 50 and lower partially circular arm extensions 52, along with the lower arm extension motors 54, upper arm cameras 56, and lower arm cameras 58. In FIG. 7A, the lower partially circular arm extensions 52 are fully extended, and in FIG. 7B the lower partially circular arm extensions 52 are fully retracted. Examples exist wherein arm extensions 52 are partially retracted so that cameras 58 can be selectively positioned at any angular position between the fully extended/retracted. positions of FIGS. 7A and 7B.

Figure 8:
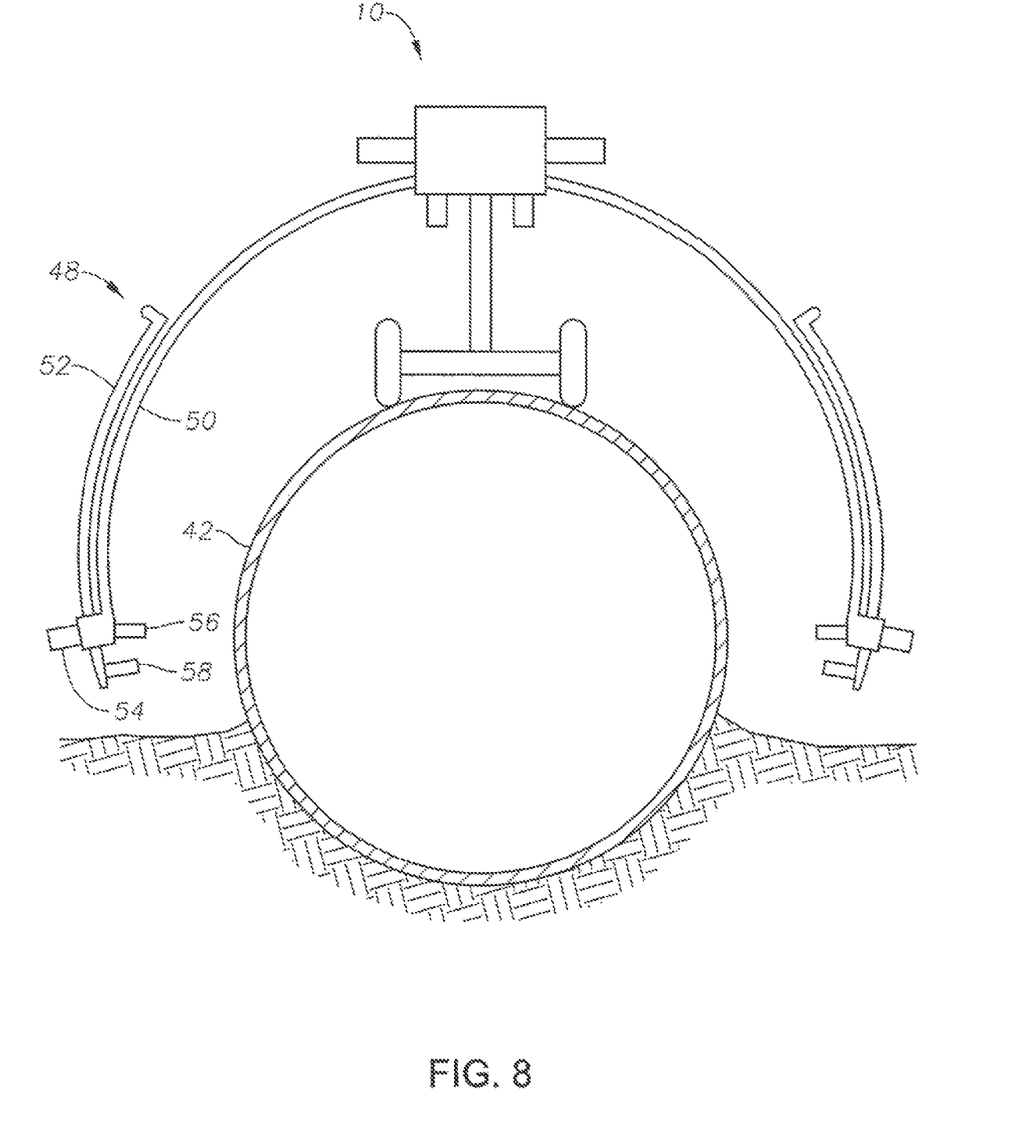
FIG. 8 is a rear elevation view of an example of the pipeline inspection robot with an optional multiple arm side extension camera system surveying a half-buried pipeline.

FIG. 8 illustrates a rear elevation view of the pipeline inspection system showing the pipeline inspection robot 10 with the optional multiple arm side extension camera system 48 surveying a half-buried pipeline 42. In this embodiment the camera system 48 can operate with the set of lower circular camera arms 52 in a partially retracted position relative to the upper circular camera arms 50. In some embodiments, lower circular camera arms 52 can telescope with hollow interiors of upper circular camera arms 50. This limits the amount of the pipeline 42 that can be surveyed but also maximizes the usefulness of the inspection robot 10 on other portions of the pipeline 42 where the pipeline 42 is not buried. When lower circular camera arms 52 are retracted, the lower cameras 58 can be turned off. The lower extension arms 52 can retract when needed and then extend again when the image analysis shows the pipeline 42 is not buried in a section.

In the event more than half of pipeline 42 is buried, the upper and lower camera arms 50, 52 can have a feature that allows the upper and lower camera arms 50, 52 to rotate about the connection with housing 12. In that event, the upper and lower camera arms 50, 52 could lift cameras 56, 58 above the pipeline 42, possibly even to a vertically upright position. Normally upper and lower camera arms 50, 52 would be retracted and cameras 56, 58 turned off when pivoted to an upward extending position.

While the technology has been described in conjunction with specific embodiments thereof it is evident that many alternatives, modifications, and variations will be apparent to those skilled in the art in light of the foregoing description. Accordingly, it is intended to embrace all such alternatives, modifications, and variations as fall within the spirit and broad scope of the appended claims. The present technology can suitably comprise, consist or consist essentially of the elements disclosed and can be practiced in the absence of an element not disclosed. Furthermore, language referring to order, such as first and second, should be understood in an exemplary sense and not in a limiting sense. For example, it can be recognized by those skilled in the art that certain steps can be combined into a single step.

The singular forms "a", "an" and "the" include plural referents, unless the context clearly dictates otherwise.

Optional or optionally means that the subsequently described event or circumstances may or may not occur. The description includes instances where the event or circumstance occurs and instances where it does not occur.

Ranges can be expressed herein as from about one particular value, and/or to about another particular value. When such a range is expressed, it is to be understood that another embodiment is from the one particular value and/or to the other particular value, along with all combinations within said range.

What is claimed is:

1. A pipe inspecting robot for traveling along the surface of a pipeline, the robot comprising:
    a body;
    first and second articulable legs that articulate independently of one another and are attached to the body, the legs articulable around the body around a common central body axis;
    first and second leg motors controlling the first and second articulating legs, respectively; and
    first and second pairs of wheels attached to the first and second articulating legs, respectively, at an opposite end of the legs from the body, the first leg articulable around the first pair of wheels around a first wheel axis, and the second leg articulable around the second pair of wheels around a second wheel axis, the first wheel axis and the second wheel axis parallel to the central body axis, and the first and second wheels configured to move along the pipeline with the body;
    the first and second leg motors configured so that when the first pair of wheels encounters an obstacle in front of the first pair of wheels in the direction of movement of the body, the second leg motor rotates the second leg upward away from the surface of the pipeline and radially around the body until the second pair of wheels contacts the surface of the pipeline on an opposite side of the obstacle, after which the first leg motor rotates the first leg upward away from the surface of the pipeline and radially around the body until the first pair of wheels contacts the surface of the pipeline, thereby causing the robot to pass over the obstacle.

2. The pipe inspecting robot of claim 1, wherein the first and second pairs of wheels are attached to the first and second articulating legs by first and second wheel hubs, respectively, and wherein the wheel hubs contain at least one wheel motor to power the wheels.

3. The pipe inspecting robot of claim 2, wherein each wheel is powered by a separate wheel motor, and wherein the course of the robot can be adjusted by increasing or decreasing the speed of each wheel with its corresponding wheel motor.

4. The pipe inspecting robot of claim 1, wherein the body contains at least one device selected from the group consisting of a control circuit, a communication circuit, a global positioning system (GPS) circuit, a GPS antenna, a camera, a camera circuit, and a battery pack.

5. The pipe inspecting robot of claim 1, further comprising:
    a downward facing camera attached to the body for collecting data about the surface condition of the pipeline and for guiding the robot.

6. The pipe inspecting robot of claim 1, wherein the robot is autonomous.

7. The pipe inspecting robot of claim 1, wherein the robot is remote controlled.

8. The pipe inspecting robot of claim 1, further comprising:
    pins attached to the body and having an extended and a retracted position, wherein when in the extended position the pins lock the position of the legs relative to the body, and when in the retracted position the pins allow the legs to articulate relative to the body.

9. The pipe inspecting robot of claim 1, further comprising:
    a radial arm attached to the body and extending outward from the body around a portion of the circumference of the pipe, the radial arm having a camera for inspecting the surface of the pipe.

10. The pipe inspecting robot of claim 9, further comprising:
    a radial arm extension slidably attached to the radial arm and configured to extend still further around the circumference of the pipe.

11. A pipeline inspection robot, comprising:
    a body;
    first and second legs that articulate independently of one another, that are attached to the body, and that are articulable around a common central body axis;
    first and second wheels attached to the first and second legs, respectively, at an opposite end of the legs from the body, the first leg articulable around the first wheel around a first wheel axis, and the second leg articulable around the second wheel around a second wheel axis, the first wheel axis and the second wheel axis oriented parallel to the central body axis, and the first and second wheels configured to move along the pipeline with the body;
    the first and second legs and first and second wheels configured so that when the first wheel encounters an obstacle in front of the first wheel in the direction of movement of the body, the second leg rotates upward away from the surface of the pipeline and radially around the body until the second wheel contacts the surface of the pipeline on an opposite side of the obstacle, after which the first leg rotates upward away from the surface of the pipeline and radially around the body until the first wheel contacts the surface of the pipeline, thereby causing the robot to pass over the obstacle; and
    a radial arm attached to the body and extending outward from the body around a portion of the circumference of the pipeline, the radial arm having a camera for inspecting the surface of the pipeline.

12. The pipeline inspection robot of claim 11, further comprising:
    a radial arm extension slidably attached to the radial arm and configured to extend further around the circumference of the pipeline than the radial arm.

13. The pipeline inspection robot of claim 11, further comprising:
    first and second leg motors controlling the first and second legs, respectively, the first and second leg motors configured so that when the first wheel encounters an obstacle in front of the first wheel in the direction of movement of the body, the second leg motor rotates the second leg upward away from the surface of the pipeline and radially around the body until the second wheels contacts the surface of the pipeline on an opposite side of the obstacle, after which the first leg motor rotates the first leg upward away from the surface of the pipeline and radially around the body until the first pair of wheels contacts the surface of the pipeline, thereby causing the robot to pass over the obstacle.

14. The pipeline inspection robot of claim 11, wherein the first and second wheels are attached to the first and second legs by first and second wheel hubs, respectively, wherein the wheel hubs contain a separate wheel motor for each wheel, and wherein the course of the robot can be adjusted by increasing or decreasing the speed of each wheel with its corresponding wheel motor.

15. The pipeline inspection robot of claim 11, further comprising:
   a downward facing camera attached to the body for collecting data about the surface condition of the pipeline and for guiding the robot.

16. The pipeline inspection robot of claim 11, wherein the robot is autonomous.

17. The pipeline inspection robot of claim 11, wherein the robot is remote controlled.

18. The pipeline inspection robot of claim 11, further comprising:
   pins attached to the body and having an extended and a retracted position, wherein when in the extended position the pins lock the position of the legs relative to the body, and when in the retracted position the pins allow the legs to articulate relative to the body.

19. A method of inspecting a pipeline, the method comprising:
   providing a robot inspection device comprising:
      a body having a central body axis;
      first and second wheel assemblies having first and second wheel axes, respectively, the first and second wheel axes oriented parallel to the central body axis, the first and second wheel assemblies configured to articulate fully around a circumference of the body around the central body axis, and also to articulate around the first and second wheel axes, and having wheels on an end distal from the body, and the first and second wheel assemblies configured to move along the pipeline with the body;
   urging the device along the pipeline and adjacent to an obstacle in front of the first wheel assembly in the direction of movement of the body on the pipeline so that the first wheel assembly is proximate the obstacle;
   articulating the body with respect to the first wheel assembly around the first wheel axis, and articulating the second wheel assembly distal from the obstacle with respect to the body around the central body axis so that wheels on the second wheel assembly orbit over the pipeline and land on the pipeline on a side of the obstacle opposite the first wheel assembly; and
   articulating the body with respect to the second wheel assembly around the second wheel axis, and articulating the first wheel assembly with respect to the body around the central body axis so that wheels on the first wheel assembly land on the pipeline on a side of the second wheel assembly, and at a position distal from the obstacle.

20. The method of claim 19, further comprising:
   detecting the obstacle using a device attached to the robot body and selected from the group consisting of a camera, a global positioning system (GPS), and a proximity sensor.

* * * * *